United States Patent [19]

Spohn et al.

[11] 4,255,279
[45] Mar. 10, 1981

[54] DUAL DEMETALLING OF OXO PRODUCTS WITH CATALYST RECYCLE

[75] Inventors: Ralph J. Spohn, Baton Rouge, La.; Paul A. Ellsworth, Sandwich, Mass.; John Lyford, IV, Baton Rouge, La.

[73] Assignee: Exxon Research & Engineering Co., Florham Park, N.J.

[21] Appl. No.: 59,474

[22] Filed: Jul. 20, 1979

[51] Int. Cl.$^3$ .............. B01J 31/40; C07C 27/22; C07C 29/16; C07C 45/50
[52] U.S. Cl. .................. 252/413; 252/414; 568/454; 568/882; 568/909
[58] Field of Search .......... 252/413, 412, 414, 420; 260/604 HF; 568/909, 882, 454; 423/418

[56] References Cited

U.S. PATENT DOCUMENTS

| | | | |
|---|---|---|---|
| 2,744,936 | 5/1956 | Mertzweiller | 260/604 HF |
| 2,751,403 | 6/1956 | Mertzweiller | 260/604 HF |
| 2,757,205 | 7/1956 | Mertzweiller et al. | 260/604 HF |
| 2,757,377 | 7/1956 | Mertzweiller et al. | 260/604 HF |
| 2,767,048 | 10/1956 | Mertzweiller | 260/604 HF |
| 2,816,933 | 12/1957 | Mertzweiller | 260/604 HF |
| 3,941,848 | 3/1976 | Kummer et al. | 260/604 HF |
| 3,957,684 | 5/1976 | Strohmeyer et al. | 423/418 |
| 4,061,687 | 12/1977 | Kaufhold | 252/414 |

FOREIGN PATENT DOCUMENTS

804664 11/1974 Belgium .

OTHER PUBLICATIONS

"Organic Synthesis via Metal Carbonyls," Wender & Pino Interscience Publishers, N. Y., pp. 249-251.

*Primary Examiner*—P. E. Konopka
*Attorney, Agent, or Firm*—Rebecca Yablonsky

[57] ABSTRACT

This invention relates to a process for dual demetalling of an oxo product contaminated with cobalt-containing catalyst residues and recovering catalytically active cobalt carbonyls which comprises treating the oxo product in a first zone with an aqueous solution of a cobalt salt of an organic or inorganic acid to extract cobalt carbonyl partially from the oxo product into the aqueous phase containing $Co^{++}$ ions to form $Co[Co(CO)_4]_2$ therein and in a second zone substantially completing the demetalling of the thus treated oxo product by treatment with an aqueous organic or inorganic acid in the presence of air or oxygen to form a $Co^{++}$ salt and using the resulting aqueous solution as feed to the first zone; subjecting the aqueous phase obtained from the first zone to preforming in a high pressure preformer under synthesis gas to convert any excess or residual $Co^{++}$ salt contained in said aqueous phase to $Co[Co(CO)_4]_2$ and extracting cobalt carbonyls from the aqueous phase with an organic solvent, the organic solvent extract being recycled to the oxo reactors as catalyst.

12 Claims, 1 Drawing Figure

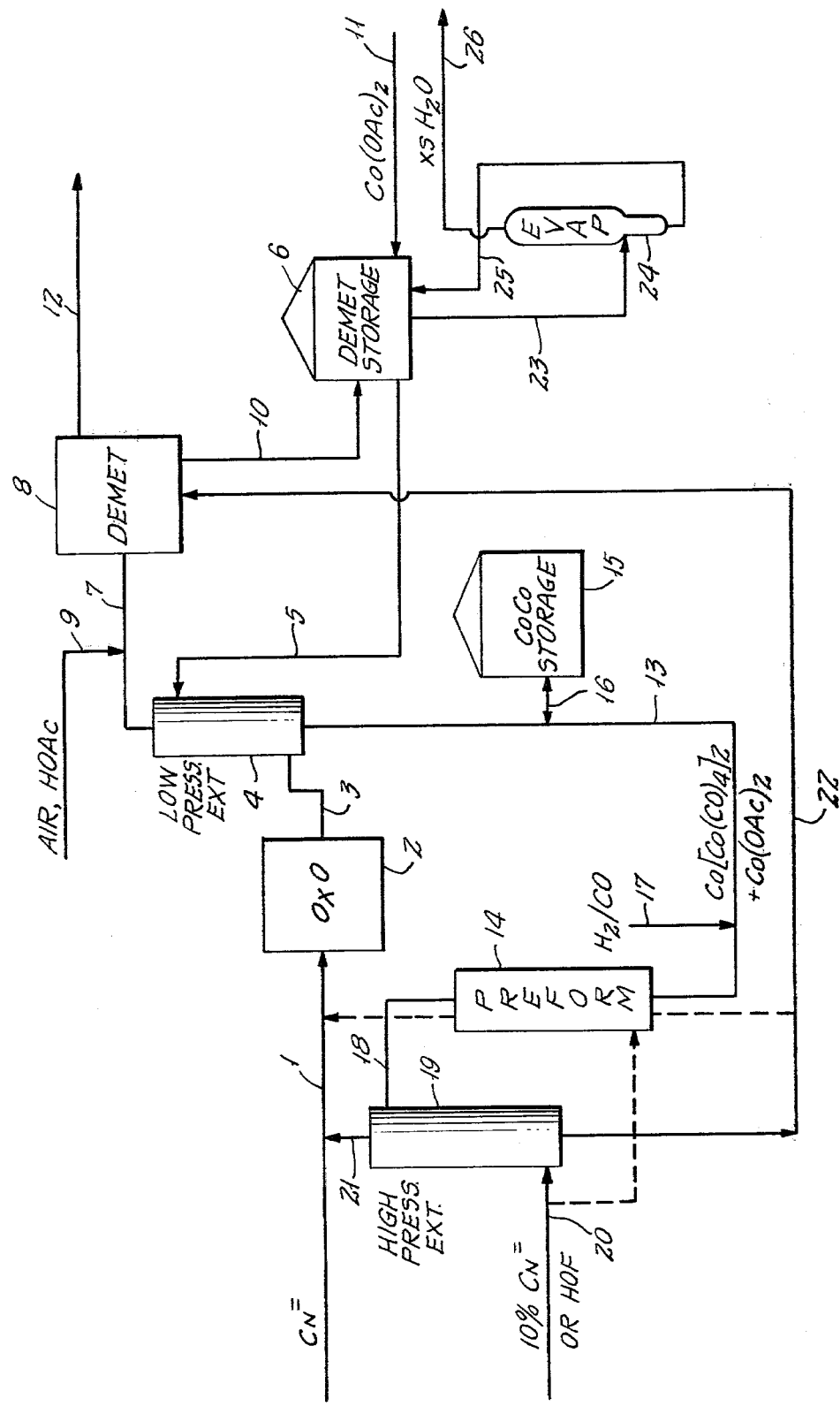

DUAL DEMETALLING OF OXO PRODUCTS WITH CATALYST RECYCLE

BACKGROUND OF THE INVENTION

1. Field of the Invention

This invention relates to the oxo process, particularly to the catalyst cycle. That is, it relates to an improved process for removing metal-containing catalyst residues, especially of metals of Group VIII of the Periodic Table, e.g., cobalt, from crude oxo reaction products, to purify the latter, and recovering such catalyst residues in a form suitable for recycle to the oxo reaction. Thus, the present invention concerns a fully integrated demetalling-catalyst recovery process wherein obtaining the catalyst in suitable form for recycling is achieved.

The oxo process is well known and involves the preparation of oxygenated organic compounds by the reaction of carbon monoxide and hydrogen (synthesis gas) with carbon compounds containing olefinic linkages in the presence of a carbonylation catalyst at hydroformylation conditions which include synthesis gas pressures of 1500 to 4500 psig and temperatures in the range of 150°–450° F.

This carbonylation reaction provides a particularly attractive method for preparing valuable primary alcohols which find large markets, particularly as intermediates for plasticizers, detergents and solvents. Amenable to the reaction are long and short chained olefinic compounds, depending upon the type alcohols desired. Not only olefins, but most organic compounds possessing at least one non-aromatic carbon-carbon double bond may be reacted by this method. Thus, straight and branch-chained olefins and diolefins such as propylene, butylene, pentene, hexene, heptene, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired.

Chief among the catalysts used has been a metallic soap, viz, cobalt oleate. However, there has been continued interest in other, lower cost alternatives to the expensive cobalt soap, which, during use, is converted to other forms that have to be reconverted to the soap.

Regardless of the catalyst used, during the process the oxo products obtained are contaminated with metal-containing catalyst residues which must be removed in order to obtain purified materials, e.g., aldehydes and, subsequently, after hydrogenation, alcohols. Because of the strategic importance and the increasing cost of cobalt, it is desirable that substantially all of the metal be recovered and reutilized.

2. Description of the Prior Art

U.S. Pat. No. 2,751,403 issued on June 19, 1956 to J. K. Mertzweiller discloses that the cobalt in a contaminated crude aldehyde oxo product can be removed by extraction with an aqueous acid such as acetic acid and that the aqueous extract will contain cobalt in both the cationic and anionic forms, viz., as the anion $[Co(CO)_4]^-$ and the corresponding cobalt salt, cobalt bis cobalttetracarbonylate, $Co^{++}[Co(CO)_4]^-_2$. The patentee subjected the aqueous extract to oxidation with the addition of, e.g., sodium oleate, to convert anionic cobalt to cobaltous ion and yield cobalt oleate, which was the desired catalytic species. U.S. Pat. No. 2,757,377 issued on July 31, 1956 to J. K. Mertzweiller et al. is similarly directed to elimination of anionic cobalt. The process involves thermal degassing of the aldehyde feed prior to the acid decobalting operation and recovering an aqueous solution of cobaltous ion which can be readily converted to the soap.

In U.S. Pat. No. 2,757,205 issued on July 31, 1956 to J. K. Mertzweiller et al., the aqueous solution containing $Co[Co(CO)_4]_2$ recovered from the catalyst removal zone is passed to the carbonylation zone to supply "at least a portion" of the catalytic requirements thereof. In U.S. Pat. No. 2,744,936 issued on May 8, 1956 to J. K. Mertzweiller, decobalting is carried out by means of an aqueous solution that provides cobaltous ions, e.g., cobalt acetate, which reacts with $[Co(CO)_4]^-$ ions present to give $Co[Co(CO)_4]_2$, the latter being passed to the carbonylation zone as catalyst.

The catalyst species is considered to be a form of the hydrido cobalt tetracarbonyl, $HCo(CO)_4$, in equilibrium with hydridocobalt tricarbonyl, $HCo(CO)_3$, according to "Organic Syntheses via Metal Carbonyls," Wender and Pino, Interscience Publishers, Volume 1, pp. 249-251.

DT-AS No. 2,244,373 to Badische Anilin & Soda-Fabrik Akt. filed on Sept. 9, 1972, describes a process which consists essentially of:

(a) demetalling the crude oxo product with an aqueous solution of an organic or an inorganic acid and oxygen to obtain the aqueous solution of a cobalt salt, e.g., cobalt acetate, formate, butyrate, chloride or nitrate;

(b) contacting the aqueous solution of the cobalt salt formed in step (a) with an organic solvent, e.g., alcohols or aldehydes, which solvent contains cobalt carbonyls, in the presence of synthesis gas at a pressure in the range of 50 to 500 atmospheres and at a temperature ranging from 50° C. to 500° C., in order to convert the water-soluble cobalt salt to hydridocobalttetracarbonyl; and, thereafter, (c) continuously recycling the organic solvent, which contains cobalt carbonyls, in a closed loop to step (b) in order to continuously convert the aqueous cobalt salt to hydridocobalttetracarbonyl, the aqueous phase containing the latter and gas phase in which it may be present, constituting the recovered catalyst.

As can be seen from the steps outlined above, characteristic features of the BASF process are that it initially obtains the catalyst residues from the oxo product entirely as the inactive $Co^{++}$ salt and continuously recycles an organic solvent in which a content of $Co^-$ has been build up to trigger the autocatalytic conversion of $Co^{++}$ to $Co^{-1}$ in a separate preforming step (b). Thus there is no conservation of the active form of cobalt present in the metal-containing crude oxo product, whereas this is achieved by means of the subject invention.

An important distinction over this reference is that the patentee starts from a condition of zero content of cobalt carbonyls and must first preform 100% of the amount needed as catalyst to get the preforming reaction going, which is more difficult than if some were already present; whereas in the present process cobalt carbonyls extracted from the oxo products and preserved are available so that the preforming reaction is ready to convert only that $Co^{++}$ which is present in excess of the $Co^{++}$ in $Co^{++}[Co^-(CO)_4]_2$.

U.S. Pat. No. 3,941,848 issued on Mar. 2, 1976, also assigned to BASF, has the same disadvantage described above. In addition it employs a heterogeneous catalyst for the preforming step such as activated carbon, zeolites and ion exchange resins impregnated with cobalt carbonyls whereas the present process utilizes a water soluble cobalt carbonyl compound as homogeneous catalyst for that purpose.

SUMMARY OF THE INVENTION

The present invention involves dual demetalling steps, that is, in the first step the crude oxo product is treated with an aqueous solution of a cobalt salt such as cobalt acetate to form from a portion of the $HCo(CO_4)$ in the oxo product, products including the salt $Co[Co(CO)_4]_2$; in the second step the so treated crude oxo product is treated with water, oxygen and an organic or inorganic acid such as acetic acid to produce the aqueous cobalt salt, called demet water, which is employed as reagent in the first step, and substantially completely demetalled oxo product.

Without wishing to be bound by theory, applicants believe that the reactions taking place may be illustratively depicted as follows:

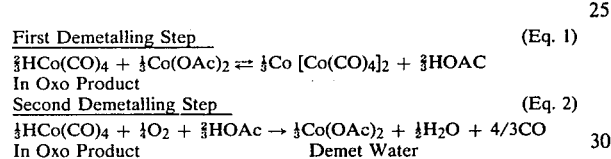

Equation 1 describes the ideal case. In practice an excess of $Co^{++}$ over that needed for $Co[Co(CO)_4]_2$ formation can be expected. Then the aqueous phase from the first demetalling step containing excess $Co^{++}(OAc)^-{}_2$ is treated with synthesis gas at elevated temperature and pressure in a high pressure reactor to effect the conversion of the excess cobaltous salt contained therein to the carbonyl form. The aqueous effluent of this step is brought into contact with a suitable organic solvent at elevated pressure to extract the cobalt carbonyls into the organic solvent phase and the latter is introduced into the oxo reactors as catalyst.

BRIEF DESCRIPTION OF DRAWING

The FIGURE is a flow diagram illustrating the process.

DETAILED DESCRIPTION

One difficulty in recycling an aqueous stream of $Co[Co(CO)_4]_2$ to the oxo reactors as catalyst, as disclosed in U.S. Pat. No. 2,757,205, involves the constraints imposed by solubility limits. The first of these constraints is the very low solubility of water in the feed olefin and in the various organic phases in the reactor beds and cooling liquid recycle streams. The second of these is the solubility of the aforesaid cobalt salt in water, about 7-10 weight percent (wt. % Co). This means that only a relatively small amount of cobalt can be introduced without the risk of flooding the reactors, as discussed in the above patent. An important advantage of the present invention over these patents is that it permits addition of recycle catalyst in an active non-aqueous form to the oxo reaction.

More specifically, the subject invention may suitably be carried out by means of the following steps:

(a) extracting preferably a major amount, i.e., more than half, for example about two-thirds of $HCo(CO)_4$ dissolved in the crude oxo product with an aqueous solution containing a $Co^{++}$ salt of an organic or inorganic acid, e.g., cobalt acetate, in the presence of an inert gas such as $N_2$ or preferably of synthesis gas, at about atmospheric pressure to about 200 psig, to form products including $Co^{+2}[Co^{-1}(CO)_4]_2$ which contains two-thirds of its cobalt as $Co^-$, i.e., the anion of an active form of the cobalt carbonyl catalyst;

(b) separating the mixture obtained in step (a) into an aqueous layer containing water-soluble $Co[Co(CO)_4]_2$ plus excess $Co(OAc)_2$, and an oil-phase oxo product which contains the remaining, e.g., about one-third, $HCo(CO)_4$;

(c) treating the approximately one-third $HCo(CO)_4$ remaining in the partially demetalled oxo product separated in step (b) in the presence of air or oxygen with an aqueous solution of an acid such as formic, propionic, e.g., acetic acid to form $Co(OAc)_2$;

(d) separating as by settling the mixture of step (c) to recover the substantially completely demetalled oxo product and an aqueous layer containing a salt, e.g., $Co(OAc)_2$, and using this demet water as feed to step (a);

(e) treating the aqueous solution of $Co[Co(CO)_4]_2$ containing any excess $Co(OAc)_2$ produced in step (b) with synthesis gas at a pressure in the range of from about 1500 to about 4500 psig and at a temperature in the range of from about 100° to about 400° F.;

(f) contacting the aqueous effluent of step (e) now containing just the $Co[Co(CO)_4]_2$ salt with an organic solvent at elevated pressure to extract the cobalt carbonyls; and (g) passing the organic solvent extract to the oxo reactors as catalyst.

As a modification of the above, steps (e) and (f) may be combined, that is, the organic solvent may be introduced directly into the preforming reactor and withdrawn therefrom for passage to the oxo reactors. It is also within the scope of the present invention under certain circumstances to bypass the preforming reactor and pass the aqueous phase from the first demetalling step obtained in step (b) directly into contact with the organic solvent for extraction of cobalt carbonyls. These circumstances may occur for instance when demetalling operations are close to ideal and the aqueous phase from the first demetalling step contains so small an excess of cobaltous salt such as cobalt acetate that maximizing the content of $Co[Co(CO)_4]_2$ of said phase by passing it through the preformer is not worthwhile; or when it contains $HCo(CO)_4$ rather than excess cobaltous salt.

At the very start of the oxo plant operation, i.e., before there is any recycle catalyst in existence, a conventional catalyst such as a cobalt soap may be used and then phased out.

Make-up cobalt may be needed because some thermal degradation of $HCo(CO)_4$ may occur in the process so that it does not operate at 100% efficiency. Depending on operating conditions in the oxo unit, the amount of make-up that must be added from an outside source typically ranges from 0-10% of total cobalt employed. A simple and convenient way of accomplishing this is to add further cobalt salt, e.g., a soluble salt, such as the acetate, formate, or the like, to the demet water, which will be processed as any other portion of demet water.

The extraction of the $HCo(CO)_4$ from an oxo product is controlled by three variables: temperature, pressure and the water/oil phase volume ratio but not by $Co^{++}$ concentration in the demet water which may be varied widely. Highly efficient removal of hydridocobaltcarbonyl from oxo product is feasible under mild conditions.

The conditions suitable in the first demetalling step are as follows:

| Parameter | Range | Preferred |
|---|---|---|
| Temperature | 50° to 200° F. | About 150° F. |
| Pressure | ~Atmospheric to 200 psig | About 50 psig |
| Moles $Co^{+2}$/Moles Co in Oxo Product | 0.1 to 2 | |
| Water/Oxo Product Phase Ratio by volume | 0.005 to 0.5 | 0.02 to 0.16 |
| Synthesis Gas Composition | 40–60% CO: 60–40% $H_2$ | |

The extraction of hydridocobalttetracarbonyl increases, within these ranges, with increasing temperature and decreasing synthesis gas pressure and with increasing water/oil phase ratio.

The conditions suitable in the second demetalling step are the following:

The oxo product is treated with oxygen or air, an organic acid such as acetic acid, and water, suitably at a temperature in the range of about 150° to about 200° F.

The cationic cobalt salt formed in the second demetalling step is soluble in water and thus can be separated from the organic layer, resulting in a Co concentration of about 10 ppm or less in the oxo product.

Advantageously the subject dual demetalling procedure preserves a substantial amount of the anionic cobalt contained in the oxo product and yet is as efficient as a single demetalling step (with $H_2O$, air and HOAc) in removing cobalt from the aldehydes. On the contrary, such a single demetalling oxidizes all the $Co^-$ to $Co^{++}$.

The aqueous phase from the extraction step described in paragraphs (a) and (b) containing cobaltous acetate and $Co[Co(CO)_4]_2$ is treated with a mixture of hydrogen and carbon monoxide at elevated temperatures and pressures in a preforming step to effect the conversion of a portion of the cobaltous salt to the carbonyl form. The $Co[Co(CO)_4]_2$ which is present in the aqueous solution acts as a homogeneous catalyst for the conversion of the cobaltous salt. A maximum of about 67% of the total cobalt in the solution can exist in the carbonyl form at the conclusion of the preforming step, as shown by the exemplifying reaction which occurs during this step:

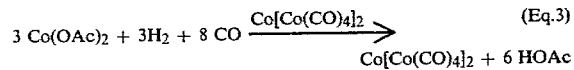

$$3\ Co(OAc)_2 + 3H_2 + 8\ CO \xrightarrow{Co[Co(CO)_4]_2} Co[Co(CO)_4]_2 + 6\ HOAc \quad (Eq.3)$$

The appropriate conditions for this step of the process are:
Temperature: 100°–400° F.
Pressure: 1500–4500 psig
Gas Compositions: 40–60% CO, 60–40% $H_2$ The aqueous effluent from the preforming step is treated with a suitable hydrocarbon at elevated pressures to extract the cobalt carbonyls into the hydrocarbon phase. One type of appropriate hydrocarbon for this extraction is the olefin which will be the feed to the oxo reactors. Appropriate conditions for this extraction step are:
Temperature: Ambient–350° F.
Pressure: 1500–4500 psig
Vol. hydrocarbon/vol. of aqueous preformer product: 1:10 to 10:1

It should be noted that Equation (1) is an equilibrium reaction which, in its reverse aspect, regenerates hydridocobaltcarbonyl. However, the equilibrium greatly favors the $Co[Co(CO)_4]_2$ form. Nevertheless by removing the hydridocobaltcarbonyl from the aqueous phase, into an organic phase, one can make the reverse reaction progress. This is essentially what is accomplished in the high pressure extraction with an organic solvent, whether in a separate extraction step or in the preformer itself.

The organic extracting liquid may be selected from U.O.P. olefins, the feed olefins, hydroformylation product from any stage, the heavy oxygenated fraction (HOF) bottoms from the distillation or demetalled oxo alcohol product, or other suitable oxygenated solvents alone or in combination. U.O.P. olefins are defined in U.S. Pat. No. 4,078,132.

As shown in the FIGURE, an olefin feed $C_N=$ which may be for example a U.O.P. olefin such as $C_9=$ or $C_{12}=$ is passed via line 1 into the oxo reactors 2 and caused to react with synthesis gas under hydroformylation conditions to form oxygenated products contaminated with metal-containing catalyst residues. The crude oxo product containing the active hydridocobalttetracarbonyl catalyst is passed through line 3 into the low pressure extractor or first demetalling zone 4, where it is well mixed with a sufficient quantity of demet water, i.e., an aqueous cobalt salt, vis., cobalt acetate passed thereinto by line 5 from demet storage facility 6 to react with, for example, about ⅔ of the cobalt content of the crude oxo product, thereby ideally forming $Co[Co(CO)_4]_2$ in the aqueous phase of which ⅓ is present as $Co^{++}$ and ⅔ as $Co^{-1}$. The water phase now containing the extracted catalyst is separated from the organic phase by settling. The remaining oxo product now containing about ⅓ of the original amount of cobalt, is passed by line 7 into the second demetalling zone 8 where the remaining cobalt is removed by contacting with oxygen or air, acetic acid or other suitable acid and water introduced through line 9. Demet water may be passed via line 10 to demet storage 6 and additional cobalt acetate supplied thereto by line 11 as needed for make-up. The reaction products in zone 8 are separated by settling. Conventional mixer-settler equipment may be used throughout. Separation produces the feed stream, i.e., the demet water for the first demetalling zone 4 which is passed thereto by lines 10 and 5; and the demetalled oxo product which is recovered through line 12. The aqueous phase containing $Co[Co(CO)_4]_2$ and $Co(OAc)_2$ is passed from extractor 4 via line 13 to the high pressure preformer 14. A storage facility 15 and line 16 may suitably be provided to receive or to furnish this aqueous mixture. Synthesis gas is supplied to preformer 14 by lines 17 and 13. The aqueous effluent from preformer 14 is passed via line 18 to high pressure extractor 19 also operated under a pressure of synthesis gas. A suitable organic solvent such as a portion, e.g. 10%, of olefin feed or HOF bottoms is passed into the extractor 19 by line 20 and the resulting organic extract containing cobalt carbonyls is separated and introduced into the oxo reactors 2 via lines 21 and 1 as catalyst. (This organic phase need not, and in most cases will not, constitute the entire organic material charged to these reactors). Changes in catalyst concentration in the organic phase are effected by varying the organic to aqueous phase ratio in extractor 19 as needed to provide the desired cobalt catalyst concentration in the organic phase. Alternatively, the organic solvent may be introduced directly into the preformer 14 as shown by the dotted lines and the high pressure extractor 19 and its piping may be eliminated. The resulting aqueous phase is passed by line 22 to the second demetalling zone 8 and it circulates in the system in a closed loop. It may be noted at this point that there is no discarding of this circulating stream, which both conserves cobalt and avoids pollution. However, if excess water accumulates, it may be removed by withdrawing a side stream 23 from demet storage 6, evaporating a portion of the water in evaporator 24, returning the stream to storage via line 25 and removing the evaporated water from the system by line 26.

The invention is illustrated by the following examples.

EXAMPLE 1A

Oxo Reaction with Cobalt Carbonyls as Catalyst

The autoclave charge was prepared by dissolving 4.65 g of dicobalt octacarbonyl, $Co_2(CO)_8$, in solid form in 800 g of UOP nonene which had been freshly sparged with nitrogen. This solution, containing 0.20 wt. % Co on olefin, was then drawn into an evacuated bomb and transferred to a 3 liter autoclave with nitrogen. The autoclave was purged twice, pressurized to 2500 psig with synthesis gas (40% CO, 60% $H_2$) and heated to 325° F. (163° C.). It may be noted that $Co_2(CO)_8$, on being pressurized with synthesis gas, forms the hydridocobaltcarbonyl, $HCo(CO)_4$.

When the initial uptake of synthesis gas was observed, the pressure was increased to 3000 psig. The reaction was allowed to proceed for 90 minutes at 325° F. and then halted by rapid cooling to 150° F. (65.6° C.).

A typical reaction resulted in an oxo product containing 11.2% light ends, 23.0% aldehydes, 26.1% alcohol, 8.3% ether, 27.4% acetal, 4.0% heavy ends and 0.14 wt. % Co.

EXAMPLE 1B

Catalyst Extraction Into an Aqueous Phase in First Demetalling Step

A series of experiments was performed to evaluate the effect of changes in temperature and pressure on the amount of hydridocobalttetracarbonyl extracted from oxo product. The volume of the aqueous extraction solution was kept constant at two volume percent of the olefin feed (to the oxo reactors). It contained enough cobalt acetate to remove theoretically 67% of the oxo catalyst as $Co[Co(CO)_4]_2$. The extracting solvent also contained sufficient acetic acid to approximate the 50% excess acetic acid that is normally found in demet water.

The results of these experiments can be seen in Table I. There was a marked increase in extraction of oxo catalyst when the extraction pressure was reduced from 200 to 50 psig synthesis gas. This increase in catalyst extraction was observed at both 150° and 180° F. with optimum extraction occurring at 180° F.

All of the extractions were run with either 0.28 g or 0.45 g of $Co^{+2}$ in the extracting solvent. An appropriate weight of stock solution was measured into a dropping funnel and then diluted with an appropriate weight of distilled water that had been freshly sparged with nitrogen. The extracting solvent was placed in the autoclave and the mixture with the oxo product stirred for 10 minutes. The extraction mixture was then held for 10 minutes without stirring to permit complete phase separation.

The data in Table I demonstrate that 67% of the hydridocobaltcarbonyl can be extracted under low pressure and moderate temperature in a single extraction of 2 liquid volume % water. At 180° F. and 50 psig, 74% of the hydridocobaltcarbonyl is extracted.

The thus treated oxo product was successfully completely demetalled with air, water and acetic acid to a cobalt content of about 10 ppm.

TABLE I

| EXTRACTION OF HYDRIDOCOBALTCARBONYL FROM $C_{10}$ OXO PRODUCT - TEMPERATURE AND PRESSURE EFFECTS | | | | | | |
|---|---|---|---|---|---|---|
| | Extractions at 150° F. | | | Extractions at 180° F. | | |
| Run No. | 1 | 2 | 3 | 4 | 5 | 6 |
| Extraction Pressure (Synthesis Gas) psig | 50 | 110 | 200 | 50 | 100 | 200 |
| $Co^{-1}$ Extracted | | | | | | |
| From oil analyses only (wt. %) | 67.5 | 43.0 | 38.0 | 73.1 | 59.8 | 55.6 |
| From oil and $H_2O$ analyses (wt. %) | 65.1 | 45.6 | 41.7 | 74.3 | 57.4 | 52.4 |
| Cobalt in Aqueous Extract | | | | | | |
| $Co^{+2}$ before extraction (g) | 0.286 | 0.288 | 0.286 | 0.286 | 0.286 | 0.453 |
| $Co^{-1}$ after extraction (g) | 0.462 | 0.360 | 0.273 | 0.536 | 0.443 | 0.409 |
| Cobalt in Oxo Product | | | | | | |
| $Co^{-1}$ before extraction (g) | 0.710 | 0.790 | 0.654 | 0.721 | 0.772 | 0.781 |
| $Co^{-1}$ after extraction (g) | 0.231 | 0.444 | 0.406 | 0.194 | 0.310 | 0.347 |
| Oxo Product GC Analysis | | | | | | |
| Light ends (%) | 11.5 | 12.3 | 11.4 | 11.7 | 11.0 | 10.1 |
| Aldehyde (%) | 26.4 | 26.1 | 24.9 | 28.3 | 28.7 | 17.9 |
| Alcohol (%) | 24.8 | 23.0 | 26.4 | 30.3 | 25.8 | 33.6 |
| Ether (%) | 7.4 | 7.6 | 8.3 | 8.2 | 7.5 | 9.8 |
| Acetal (%) | 27.5 | 29.0 | 27.1 | 20.4 | 26.4 | 27.4 |
| Heavy ends (%) | 2.4 | 2.0 | 1.9 | 1.0 | 0.6 | 1.2 |

EXAMPLE 2

Preforming

The pilot unit consisted of two stirred reactors, R-1 and R-2, operating in series. A series of samples gave the results shown in Table II.

TABLE II

Aqueous Preforming of Demet Water

| Sample No. | Total Co | R-1 Co as Carbonyl | % of Theoretical Yield of Co as Carbonyl | Total Co | R-2 Co as Carbonyl | % of Theoretical Yield of Co as Carbonyl** |
|---|---|---|---|---|---|---|
| 1 | 0.4913 | 0.1125 | 34.3 | 0.4647 | 0.3175 | 102.5 |
| 2 | — | — | — | 0.4607 | 0.1986 | 64.7 |
| 3 | 0.4810 | 0.1141 | 35.6 | — | — | — |
| 4 | — | — | — | 0.4657 | 0.2203 | 71.0 |
| 5 | 0.4810 | 0.1276 | 39.8 | — | — | — |
| 6 | — | — | — | — | 0.2067 | 67.4* |
| 7 | — | 0.1167 | 38.1* | — | — | — |

Feed Analysis: Total Co 0.4597
Co as carbonyl 0

Conditions: 340° F.
3500 psig
39.3% CO, 60.7% $H_2$
Feed 0.67# $H_2O$/hr

*Yield based upon feed analysis
**Based on Eq. 3. Yields in excess of 100% mean that $HCo(CO)_4$ is also present.

EXAMPLE 3

The following example in table form shows the effect of solvent type, temperature and pressure, on the equilibrium distribution of $HCo(CO)_4$ between oil and water.

TABLE III

| Solvent | Synthesis Gas Pressure (psig) | Temperature (°F.) | $K_D$ (Oil/Water) | |
|---|---|---|---|---|
| HYDROCARBONS | | | | |
| n-heptane | 0 | 77 | 0.03 | 0.02 |
| | 1000 | 77 | 0.44 | 0.30 |
| | 3000 | 77 | 1.09 | 0.74 |
| | 3000 | 177 | 1.17 | 0.80, 0.54 |
| UOP $C_7^=$ | 0 | 77 | 0.04 | |
| | 1000 | 77 | 0.59 | |
| | 3000 | 77 | 1.55 | 0.82 |
| UOP $C_8^=$ | 3000 | 77 | — | 0.68 |
| OXO ALCOHOLS | | | | |
| i-$C_4$OH | 0 | 77 | 13 | — |
| | 1000 | 77 | 21 | — |
| | 3000 | 77 | 27 | 22 |
| | 1000 | 177 | 18 | — |
| | 3000 | 177 | 31 | — |
| i-$C_8$OH | 0 | 77 | 0.10 | — |
| | 1000 | 77 | 0.53 | — |
| | 3000 | 77 | 1.9 | 1.5 |
| | 3000 | 177 | 7.2 | — |
| $C_{10}$OH | 3000 | 77 | — | 1.1 |
| $C_{13}$OH | 3000 | 77 | — | 1.0 |
| OXO ALDEHYDES | | | | |
| i-$C_8$HO | 0 | 77 | 0.07 | — |
| | 1000 | 77 | 0.75 | — |
| | 3000 | 77 | 2.6 | — |
| $C_{10}$HO | 50 | 150 | | 0.25 |

Thus by means of the present invention the need for a separate catalyst plant, viz., for manufacturing Co oleate in which expensive oleic acid is required on a once-through basis, and which may be a bottleneck in the oxo process, is avoided. By using a dual demetalling procedure not only is demetalling of crude oxo product achieved efficiently but also active catalyst in the oxo product is extracted and preserved, then used as catalyst in a preforming step so that there is no difficulty or induction period in achieving preforming as when the starting point is an inactive cobaltous salt. Furthermore, even though this invention involves recovery and recycling of catalyst, when make-up cobalt is needed this can still be supplied without resort to cobalt soap simply by introducing the required amount of a cobaltous salt of an organic or inorganic acid and processing it along with other similar material. Additionally, the present invention operates on a closed cycle, with no side products other than water being discharged from the system, so that there are no costs due to environmental protection systems and no adverse effect on the environment. Finally, corrosion concerns associated with any catalyst cycle in which an aqueous cobalt solution is directly injected into the oxo reactors, are eliminated.

What is claimed is:

1. A process for demetalling an oxo product contaminated with cobalt-containing catalyst residues and recovering cobalt carbonyls therefrom which comprises treating the oxo product in a first demetalling zone with an aqueous solution of a $Co^{++}$ salt of an organic or inorganic acid to extract a portion of the cobalt carbonyl from the oxo product into the aqueous phase and to form products including $Co[Co(CO)_4]_2$ therein and in a second demetalling zone substantially completing the demetalling of the thus treated oxo product by treatment with an aqueous organic or inorganic acid in the presence of oxygen to form a $Co^{++}$ salt of said acid and using the resulting aqueous solution (demet water) as feed to said first demetalling zone; treating said aqueous phase with synthesis gas in a high pressure reactor at a pressure in the range of from about 1500 psig to about 4500 psig and at a temperature in the range of from about 100° to about 400° F.; contacting the aqueous effluent thereof with an organic solvent at elevated pressure to extract cobalt carbonyls; and passing the organic solvent extract to the oxo reactors as catalyst.

2. A process according to claim 1 wherein in the first demetalling zone the temperature is in the range of about 50° to about 200° F. and the pressure is in the range of about atmospheric to about 200 psig.

3. A process according to claim 1 in which the treatment in the high pressure reactor and the extraction with the organic solvent are carried out in separate vessels.

4. A process according to claim 1 in which the organic solvent is contacted with said aqueous phase in said high pressure reactor and the organic solvent extract is passed to the oxo reactors as catalyst.

5. A process according to claim 3 in which the aqueous raffinate from the extraction with the organic solvent is passed to the second demetalling zone and circulates in the system in a closed loop.

6. A process according to claim 1 in which said $Co^{++}$ salt is cobalt acetate or cobalt formate or mixtures thereof.

7. A process according to claim 3 in which the organic solvent is selected from the group consisting of U.O.P. olefins, the feed olefins, hydroformylation product, the heavy oxygenated bottoms fraction from the distillation of oxo alcohols and mixtures thereof.

8. A process according to claim 7 in which the organic solvent is a portion of the feed olefins.

9. A process according to claim 3 in which the extraction with the organic solvent is carried out in the presence of synthesis gas at a pressure in the range of about 1500 to about 4500 psig at a temperature of ambient to about 350° F. and with a ratio by volume of organic/aqueous of about 1:10 to 10:1.

10. A process according to claim 1 in which make-up cobalt is supplied in the form of a $Co^{++}$ salt of an organic or inorganic acid and is added to the demet water.

11. A process for demetalling an oxo product contaminated with cobalt-containing catalyst residues and recovering cobalt carbonyls therefrom which comprises in combination the following steps:

(a) extracting a portion of the $HCo(CO)_4$ dissolved in the crude oxo product with an aqueous solution of cobalt acetate in the presence of synthesis gas to form $Co[Co(CO)_4]_2$;

(b) separating the mixture obtained in step (a) into a aqueous layer containing water-soluble $Co[Co(CO)_4]_2$ and an oil-phase oxo product;

(c) treating the partially demetalled oxo product separated in step (b) with an aqueous solution of acetic acid under oxidizing conditions to form $Co(OAc)_2$;

(d) separating the mixture of step (c) to recover the demetalled oxo product and an aqueous layer containing $Co(OAc)_2$ (demet water) and using the latter as feed to step (a);

(e) passing the aqueous solution produced in step (b) with synthesis gas to a high pressure preforming reactor and subjecting the same to a pressure in the range of from about 1500 to about 4500 psig and a temperature in the range of from about 100° to about 400° F. to convert any excess $Co(OAc)_2$ to $Co[Co(CO)_4]_2$;

(f) passing the aqueous effluent from the preforming reactor, synthesis gas and an organic solvent to a high pressure extractor and carrying out extraction of cobalt carbonyls into the organic solvent at a temperature in the range of ambient to about 350° F., a pressure in the range of about 1500 to about 4500 psig and a ratio by volume of organic solvent/aqueous effluent of about 1:10 to 10:1; and (g) passing the organic solvent extract into the oxo reactors as catalyst.

12. A process according to claim 11 in which the organic solvent consists of about 10% of the total olefin feed used for the oxo reaction.

* * * * *